United States Patent [19]

Miyata et al.

[11] Patent Number: 4,576,819

[45] Date of Patent: Mar. 18, 1986

[54] ALUMINUM HYDROXIDE GEL, PROCESS FOR PRODUCTION THEREOF, AND USE THEREOF

[75] Inventors: Shigeo Miyata; Tsutomu Nosu, both of Takamatsu, Japan

[73] Assignee: Kyowa Chemical Industry Co., Ltd., Tokyo, Japan

[21] Appl. No.: 554,164

[22] Filed: Nov. 22, 1983

Related U.S. Application Data

[63] Continuation of Ser. No. 249,454, Mar. 31, 1981, abandoned.

[51] Int. Cl.$^4$ .............................................. A61K 33/10
[52] U.S. Cl. .................................................... 424/156
[58] Field of Search ......................................... 424/156

[56] References Cited

U.S. PATENT DOCUMENTS

| | | |
|---|---|---|
| 2,880,136 | 3/1959 | Gore ..................................... 424/156 |
| 2,958,626 | 11/1960 | Schenck et al. ..................... 424/156 |
| 3,099,554 | 7/1963 | Grossmith ........................... 424/156 |
| 3,239,446 | 3/1966 | Rubino ................................ 424/156 |
| 3,272,773 | 9/1966 | Rubino et al. ...................... 424/156 |

Primary Examiner—Frederick E. Waddell
Attorney, Agent, or Firm—Wenderoth, Lind & Ponack

[57] ABSTRACT

An aluminum hydroxide gel of the following formula

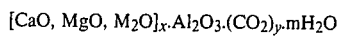

$$[CaO, MgO, M_2O]_x \cdot Al_2O_3 \cdot (CO_2)_y \cdot mH_2O$$

wherein M represents an alkali metal, $M_2O$ may be zero, CaO and MgO are not zero at the same time, and x, y and m are positive numbers represented by the following expressions $$0 < x < 1,$$

$$0.2 < y \leqq 1,$$

$$2 \leqq m < 10.$$

Said aluminum hydroxide gel can be produced by reacting an aluminum compound soluble in water and/or lower alcohols with a carbonate ion yielding compound soluble in water and/or lower alcohols at a pH of about 6 to about 9.5 under such conditions that the $CO_2/Al$ mole ratio of the resulting aluminum hydroxide gel is at least about 0.1, and ion exchanging the alkali metals of the resulting compound with magnesium and/or calcium. This invention also provides an antacid composition comprising said aluminum hydroxide gel as an active ingredient.

2 Claims, No Drawings

ALUMINUM HYDROXIDE GEL, PROCESS FOR PRODUCTION THEREOF, AND USE THEREOF

This application is a continuation of now abandoned application Ser. No. 249,454, filed Mar. 31, 1981.

This invention relates to an aluminum hydroxide gel not heretofore described in the literature, a process for production thereof, and to utilization thereof.

The novel aluminum hydroxide gel shows improved properties over known aluminum hydroxide gels in that it has a high rate of reaction with gastric acid and excellent resistance to aging, and is not likely to induce side-effects. The aluminum hydroxide gel is useful not only as an antacid but also in other applications such as an acid adsorbent and a cation exchanging agent, but much improvement is desired in its use as an antacid.

More specifically, this invention relates to an aluminum hydroxide gel of the following formula (I)

$$(CaO, MgO, M_2O)_x \cdot Al_2O_3 \cdot (CO_2)_y \cdot mH_2O$$

wherein M represents an alkali metal such as Na and K, $M_2O$ may be zero, CaO and MgO are not zero at the same time, and x, y and m represent positive numbers represented by the following expressions $0 < x < 1$, $0.2 < y \leq 1$, $2 \leq m < 10$, a process for its production, and also to an antacid composition comprising the compound of formula (I) as an active ingredient.

Aluminum hydroxide gel is a typical antacid which now gains most widespread use mainly because it induces least side-effects. Conventional aluminum hydroxide gels have the disadvantage of slow rates of reaction with acids. Furthermore, they undergo oxidation relatively rapidly after production, and in administration, a period of more than about 10 hours is required for it to neutralize gastric acid to a pH of at least 3 which is a level required of antacids. In addition, the amount of acids they neutralize is low, and their function is as an antacid is not entirely satisfactory.

Antacids are required to neutralize rapidly gastric acid having a pH of about 1.2 to about 3 to a pH of about 3 to about 5, and retain this function for an extended period of time after preparation (aging resistance). However, conventional aluminum hydroxide gels are unsatisfactory in regard to the rate of reaction with acids, aging resistance and the amount of acids neutralized, etc. as mentioned above.

We have now found that the aluminum hydroxide gel of formula (I) not described in the literature can exist and can be produced easily. It has also been found that this novel aluminum hydroxide gel exhibits a markedly increased rate of reaction with acids and markedly improved aging resistance, can be used as an antacid without side-effects, and is also useful in a wide range of applications including acid adsorbents and cation exchanging agents.

A modified aluminum hydroxide gel of the following formula $$(K_2O, Na_2O)_p \cdot Al_2O_3 \cdot (CO_2)_q \cdot rH_2O$$

wherein p is a number represented by $0 < p \leq 1$, q is a number represented by $0.2 \leq q \leq 2$, and r is a number represented by $2 \leq r \leq 3$, is known as one conventional aluminum hydroxide gel. This aluminum hydrogel has an increased rate of reaction with acids and improved aging resistance (see Comparative Examples 1 and 2 given hereinbelow) over ordinary aluminum hydroxide gels.

Investigations of the present inventors have shown that the aluminum hydroxide gel of formula (I) shows a surprisingly increased rate of reaction with acids and surprisingly improved oxidation resistance over this known modified aluminum hydroxide gel (see Example 1 and Comparative Example 1 given hereinbelow).

In addition, the alkali metal content of the aluminum hydroxide gel of formula (I) can be reduced to below about 2%, and even to 0%, based on the weight of the compound of formula (I). Hence, side-effects such as renal troubles and hypertension attributed to K and Na of the known modified aluminum hydroxide gel can be advantageously avoided in the aluminum hydroxide gel of formula (I).

It is an object of this invention therefore to provide a novel aluminum hydroxide gel.

Another object of this invention is to provide a process for producing the aluminum hydroxide gel and its utilization.

The above and other objects and advantages of this invention will become more apparent from the following description.

The novel aluminum hydroxide gel of this invention has the composition of formula (I).

$$[CaO, MgO, M_2O]_x \cdot Al_2O_3 \cdot (CO_2)_y \cdot mH_2O \qquad (I)$$

M represents an alkali metal such as K and Na, $M_2O$ may be zero, and CaO and MgO are not zero at the same time, and x, y and m are positive numbers represented by the following expressions x: $0 < x < 1$, preferably $0.1 \leq x < 0.8$, more preferably $0.2 \leq x < 0.8$, especially preferably $0.4 < x < 0.6$.

y: $0.2 < y \leq 1$, preferably $0.4 \leq y \leq 0.8$, more preferably $0.6 \leq y \leq 0.8$.

m: $2 \leq m < 10$.

The alkali metal content of the compound of formula (I) is preferably not more than about 2%, more preferably not more than about 0.5%, based on the weight of the compound (I).

In using aluminum hydroxide gels as an antacid, the alkali content of the K and Na which may induce renal troubles and hypertension is required to be usually below about 3%, and its pH is required to be below about 10 (for example, see U.S. Pharmacopoeia, and British Pharmacopoeia).

In the aluminum hydroxide gel of formula (I) of this invention, the troubles associated with the high alkali metal content and the high pH can be completely avoided. Furthermore, since Ca and Mg are effective antacid components and induce very little physiological side-effects, they do not cause a trouble of side effects when used within the composition range represented by formula (I).

Furthermore, in the aluminum hydroxide gel of formula (I) in accordance with this invention, Ca and/or Mg are bonded in the compound of formula (I) by ion exchange with alkali metals, and it does not form calcium carbonate or basic magnesium carbonate. Accordingly, the compound of formula (I) is clearly distinguished from a mixture of aluminum hydroxide gel and these compounds. Furthermore, the aluminum hydroxide gel of this invention can be clearly distinguished from a known crystalline compound $NaAl(OH)_2CO_3$ (Dawsonite) in that it is a substantially amorphous compound by X-ray diffraction analysis.

It is not entirely clear why the aluminum hydroxide gel of this invention shows markedly improved reactivity with acids and aging resistance. The present inventors theorize as follows: It is to be understood however that the present invention is not limited by this theoretical elucidation.

In conventional aluminum hydroxide gels, most of carbonate ions bonded to aluminum are monovalent and therefore have a weak bonding power. Accordingly, the conventional aluminum hydroxide gels easily hydrolyzes to aluminum hydroxide during storage, and to a greater extent, under high temperature and high humidity conditions, and their antacid activity gradually decreases with time after preparation.

In contrast, in the aluminum hydroxide gel of formula (I), the carbonate ions are divalent, and therefore have an increased bonding power with respect to aluminum, and this is presumably the reason why the aluminum hydroxide gel of the invention scarcely hydrolyzes. The better hydrolysis resistance is presumably because when K and/or Na is ion-exchanged with Ca and/or Mg, the bonding power of the Ca and/or Mg is stronger, and thus the aluminum hydroxide gel has better resistance to hydrolysis. It is also believed that since Ca and/or Mg reacts with acids faster than Al, the rate of reaction with acids is faster than the conventional aluminum hydroxide gels.

The aluminum hydroxide gel of formula (I) can be produced by reacting a soluble aluminum compound and a soluble compound capable of yielding a carbonate ion at a pH of about 6 to about 9.5 under such conditions that the $CO_2/Al$ mole ratio of the resulting aluminum hydroxide gel is at least about 0.1, and ion-exchanging the alkali metals of the resulting compound with magnesium and/or calcium.

There is no particular restriction on the reaction temperature, but temperatures of about 20° to about 50° C. are preferred. In general, the amount of a carbonate ion supplied is desirably as large as possible. If it is too large, however, the content of aluminum becomes less than 40%, and therefore, the amount of an acid to be neutralized becomes undesirably small. Conversely, if the amount of a carbonate ion supplied is too small, the rate of reaction with an acid decreases and the aging resistance of the aluminum hydroxide gel is undesirably deteriorated. Accordingly, the reaction is preferably carried out while adjusting the mole ratio of a carbonate ion to aluminum supplied ($CO_2/Al$) to at least 0.1, for example to about 0.1 to about 8, preferably to about 0.5 to about 3.

The pH of the reaction system is above the pH at which a divalent carbonate ion is present and aluminum hydroxide does not easily form, and also an ion exchange reaction of the alkali metals takes place mainly by the presence of Ca or Mg while the formation of the hydroxides of Ca or Mg scarcely takes place. The pH is, for example, about 6 to about 9.5, preferably about 7 to about 9.

Aluminum salts soluble in water and/or lower alcohols are preferably utilized as the soluble aluminum compound which also denotes aluminum metal in this invention. Examples include aluminum chloride, aluminum nitrate, aluminum sulfate, aluminum metal, aluminum ammonium sulfate, aluminum bromide, aluminum fluoride, aluminum potassium sulfate, aluminum isopropoxide, sodium aluminate, potassium aluminate, and aluminum sodium sulfate.

The soluble compound capable of yielding a carbonate ion is preferably a carbonate ion yielding compound soluble in water and/or lower alcohols. Examples include alkali metal carbonates and bicarbonates such as sodium carbonate, potassium carbonate, sodium hydrogen carbonate and potassium hydrogen carbonate, carbon dioxide gas and urea.

Alkaline substances used to adjust the pH of the reaction system may be ammonia, ammonium hydroxide, sodium hydroxide, and potassium hydroxide.

The reaction between the soluble aluminum compound and the carbonate ion yielding soluble compound can be carried out in water and/or a lower alcohol as a solvent. The ion exchange reaction of the alkali metals of the resulting compound with magnesium and/or calcium can be performed by known ion-exchanging means, for example by contacting the resulting compound with an aqueous solution containing a calcium ion and/or a magnesium ion, or by forming a cake of the compound and washing it with an aqueous solution containing a calcium ion and/or a magnesium ion. There is no particular restriction on the concentration of the aqueous solution containing a calcium ion and/or a magnesium ion, but preferably, it is used in a concentration of about 0.1 to about 1 mole/liter. Examples of the soluble calcium and/magnesium compounds utilized in the formation of the aqueous solution containing a calcium ion and/or a magnesium ion include calcium chloride, calcium nitrate, calcium fluoride, magnesium chloride, magnesium nitrate, magnesium sulfate, magnesium fluoride, magnesium iodide, concentrated sea water and bittern.

The aluminum hydroxide gel of formula (I) in accordance with this invention is useful in a wide range of applications including acid adsorbents, cation exchange agents, but exhibits particularly good performance when used as an antacid.

Accordingly, the present invention also provides an antacid comprising the compound of formula (I) as an active ingredient. For example, there can be provided an antacid composition comprising an amount effective for action as a gastric antacid of the aluminum hydroxide gel of formula (I) and a pharmaceutically acceptable diluent or carrier.

The dosage form of the antacid composition of this invention is not restricted, and may, for example, include powders, granules, particles, tablets, suspensions, and syrups. As required, lubricants, disintegrants, etc. known in the field of pharmaceutical production may be included in addition to the diluent or carrier. It may also be a mixture with another drug. The amount of the compound of formula (I) is, for example, about 1 to about 88% by weight, preferably about 20 to about 80% by weight, based on the weight of the antacid composition.

The administration route of the antacid composition may be oral. The dosage may be changed properly, and is, for example, about 1 to about 20 g/day, preferaly about 2 to about 5 g/day. The compound (I) may be administered alone.

Examples of the pharmaceutically acceptable carrier or diluent include magnesium stearate, lactose, stearic acid, calcium stearate, microcrystalline cellulose, vegetable oils, or synthetic oils such as liver oil and sunflower oil, starch sodium carboxymethyl cellulose, strawberry syrup, plain syrup water and ethanol.

The following Examples illustrate specifically the aluminum hydroxide gel of the invention, its production and its antacid effect.

EXAMPLE 1

Water (about 500 ml) was put into a 1-liter cylindrical strainless steel reaction vessel equipped with an overflowing device, and strongly stirred well with a chemistirrer. The reaction vessel was charged by metering pumps with an aqueous solution of aluminum sulfate (0.9 mole/liter as $Al_2O_3$), an aqueous solution of sodium carbonate (0.6 mole/liter) and an aqueous solution of sodium hydroxide (2.0 moles/liter) which were each maintained at 30° C.±1° C. at a total flow rate of about 200 ml/min., and they were reacted for about 1 hour. The $CO_2/Al_2O_3$ ratio was maintained at 2, and the pH of the reaction system was adjusted to 7.5±0.2.

The suspension which overflowed from the reaction vessel was dehydrated under reduced pressure by a Buchner funnel to form a cake, and the cake was washed with 40 times the weight of $Al_2O_3$ of an aqueous solution of magnesium chloride (0.2 mole/liter) to perform ion exchange. The product was washed with water, and dried at about 70° C. for 20 hours.

The resulting aluminum hydroxide gel was chemically analyzed and found to have the composition of the following formula:

$$(MgO)_{0.22} \cdot Al_2O_3 \cdot (CO_2)_{0.50} \cdot 4.7H_2O$$

The resulting gel had a sodium content of 0.21%. An X-ray diffraction analysis of the gel showed it to be substantially amorphous. The gel had a refractive index, determined by the Larsen's oil dipping method, of between 1.422 and 1.443. A sodium-containing compound present in a trace in the gel had refractive index between 1.480 and 1.495. Conventional aluminum hydroxide gels have a refractive index between 1.495 and 1.720.

The resulting aluminum hydroxide gel was tested for acid reactivity and oxidation resistance in accordance with an FDA test on O.T.C. (over-the-counter) antacids. The results are shown in Table 1.

(1) Method for testing reactivity with acid

In a 100 ml beaker, 150 ml of 0.1N HCl was accurately taken. The beaker was dipped in a constant temperature vessel at 37° C. and the solution was maintained at 37° C. The solution was stirred at 240 rpm by a magnetic stirrer. The electrode of a pH meter was dipped in the solution. 0.8 g of a sample powder was added, and simultaneously, a stop watch was started. The time which elapsed until the pH of the solution reached 3 and 3.5, respectively, and the pH of the solution 10 minutes later were measured.

(2) Aging Conditions

The sample was allowed to stand at 60° C. for 7 days in a desiccator containing a saturated aqueous solution of sodium chloride. The resulting sample was subjected to the acid reactivity test described in (1) above to determine its aging resistance.

COMPARATIVE EXAMPLE 1

In the procedure of Example 1, the cake before ion exchange with magnesium chloride was washed with water and dried at 70° C. for 20 hours. The resulting product contained 5.5% of sodium. The pH, acid reactivity and oxidation resistance of the product are shown in Table 1. When the pH of the product exceeds 10, it cannot be used as an antacid. The product had a refractive index between 1.480 and 1.495.

COMPARATIVE EXAMPLE 2

The pH, acid reactivity and aging resistance of commercially available aluminum hydroxide gel were measured, and the results are shown in Table 1. This commercial product contained 0.1% of sodium.

EXAMPLE 2

An aqueous solution of aluminum sulfate (0.9 mole/liter as $Al_2O_3$), an aqueous solution of sodium carbonate (0.75 mole/liter), and an aqueous solution of sodium hydroxide (2.0 moles/liter) were reacted in the same way as in Example 1 at a reaction temperature of 35° C. while maintaining the $CO_2/Al_2O_3$ mole ratio at 3 and the pH of the reaction system to 9. The resulting precipitate was dehydrated under reduced pressure to form a cake. The cake was ion exchanged with 20 times the weight of $Al_2O_3$ of magnesium sulfate (0.5 mole/liter). The product was washed with water, and dried at about 70° C. for 20 hours. The dried product had the following chemical composition.

$$(MgO)_{0.32} \cdot Al_2O_3 \cdot (CO_2)_{0.75} \cdot 2.8H_2O$$

The sodium content of the product was 1.15%. A powder X-ray diffraction pattern of this substance showed it to be amorphous.

The acid reactivity of this product is shown in Table 1.

EXAMPLE 3

An aqueous solution of aluminum chloride (1.0 mole/liter as $Al_2O_3$) and an aqueous solution of potassium carbonate (0.5 mole/liter) were reacted in the same way as in Example 1 at a reaction temperature of 20° C. while adjusting the $CO_2/Al_2O_3$ mole ratio to 5.1 and the pH of the reaction system to 7.5±0.2.

The precipitate was dehydrated under reduced pressure to form a cake, and the cake was ion exchanged with 40 times the weight of $Al_2O_3$ of bittern obtained by an ion exchange membrane method (a mixed aqueous solution of magnesium chloride and calcium chloride: $Mg^{2+}=0.14$ mole/liter, $Ca^{2+}=0.06$ mole/liter). The product was washed with water, and dried at 70° C. for about 20 hours. The product had the following chemical composition.

$$(CaO)_{0.13} \cdot (MgO)_{0.03} \cdot Al_2O_3 \cdot (CO_2)_{0.78} \cdot 2.5H_2O$$

The product contained 0.05% of potassium. A powder X-ray diffraction of the product showed it to be amorphous. The acid reactivity of the product is shown in Table 1.

EXAMPLE 4

One liter of an aqueous solution of aluminum chloride (2 mole/liter), 4 liters of an aqueous solution of sodium carbonate (0.75 mole/liter) and 0.84 liter of an aqueous solution of sodium hydroxide (about 3.34 mole/liter) were fed into a 2-liter cylindrical reaction vessel stirred and dipped in a warm water bath at 35° C. at a flow rate of 20 ml/min., 80 ml/min., and 17 ml/min., respectively, and were reacted while maintaining the pH of the reaction system at 8.5. After the reaction, the precipitate was filtered, and washed with 4 liters of an aqueous solution of calcium chloride (0.2 mole/liter), further washed with about 2 liters of water dehydrated, and dried. This product had the following chemical composition.

$$(CaO)_{0.55} \cdot Al_2O_3 \cdot (CO_2)_{0.88} \cdot 6H_2O$$

The product contained 0.4% of sodium. A powder X-ray diffraction of the product showed it to be amorphous. The acid reactivity of the product is shown in Table 1.

TABLE 1

| | Example 1 | Comparative Example 1 | Comparative Example 2 | Example 2 | Example 3 | Example 4 |
|---|---|---|---|---|---|---|
| pH of the aluminum hydroxide gel | 9.1 | 10.2 | 7.1 | 9.6 | 8.6 | 9.5 |
| Acid reactivity (before aging) | | | | | | |
| Time until a pH of 3 was reached (seconds) | 54 | 121 | 172 | 23 | 41 | 12 |
| Time until a pH of 3.5 was reached (seconds) | 86 | 142 | 180 | 48 | 65 | 34 |
| pH after 10 minutes | 3.8 | 3.8 | 3.7 | 3.9 | 3.8 | 4.1 |
| Acid reactivity (after aging) | | | | | | |
| Time until a pH of 3 was reached (seconds) | 105 | 246 | 570 | 47 | 62 | 15 |
| Time until a pH of 3.5 was reached (seconds) | 132 | 288 | not reached | 52 | 118 | 41 |
| pH after 10 minutes | 3.8 | 3.7 | 3.8 | 3.9 | 3.8 | 4.1 |

The acid reactivity test and the aging resistance test were also performed on the products of Examples 1 to 4 and Comparative Examples 1 and 2 using an artificial gastric juice of the following formulation. The results are shown in Table 2.

| Artificial gastric juice | |
|---|---|
| 2.7 Moles/liter HCl | 240 ml |
| Sodium chloride | 2.0 g |
| Thick pepsin | 2.1 g |
| Water | balance |
| Total: | 1,000 ml |

TABLE 2

| | Example 1 | Comparative Example 1 | Comparative Example 2 | Example 2 | Example 3 | Example 4 |
|---|---|---|---|---|---|---|
| (before aging) | | | | | | |
| Time until a pH of 3 was reached (seconds) | 53 | 119 | 171 | 21 | 39 | 10 |
| Time until a pH of 3.5 was reached (seconds) | 84 | 135 | 178 | 45 | 63 | 31 |
| pH after 10 minutes | 3.8 | 3.8 | 3.6 | 3.9 | 3.8 | 4.1 |
| (after aging) | | | | | | |
| Time until a pH of 3 was reached (seconds) | 102 | 244 | 568 | 45 | 61 | 14 |
| Time until a pH of 3.5 was reached (seconds) | 130 | 285 | not reached | 49 | 116 | 39 |
| pH after 10 minutes | 3.8 | 3.7 | 3.8 | 3.9 | 3.8 | 4.1 |

EXAMPLE 5

Some examples of formulation of the antacid composition of this invention are shown.

Powder 100 g of the compound of formula (I), 10 g of powder sugar and 0.1 g of L-menthol were fully mixed.

Granules 10 g of calcium carboxylmethyl cellulose and 0.1 g of L-menthol were added to 100 g of the compound of formula (I), and the mixture was granulated in the wet state.

Suspension 7 g of the compound of formula (I) was added to a solution of 2 g of sodium carboxylmethyl cellulose in 100 ml of water. Then, 0.05 g of sodium saccharin, 0.1 g of sodium dehydroacetate and 0.2 ml of lemon essence were added, and they were uniformly mixed by a homogenizer.

Syrup 7 g of the compound of formula (I) was mixed with 1 g of sodium carboxymethyl cellulose, and 30 ml of strawberry syrup and 60 ml of plain syrup were added, and they were well mixed to form a homogeneous syrup.

What we claim is:

1. An amorphous aluminum hydroxide gel of formula (I) in which Ca and/or Mg are bonded to the compound of formula (I) by ion-exchange with an alkali metal, $$(CaO, MgO, M_2O)_x \cdot Al_2O_3 \cdot (CO_2)_y \cdot mH_2O \qquad (I)$$

wherein M represents an alkali metal, $M_2O$ may be zero, CaO and MgO are not zero at the same time and x, y and m are positive numbers represented by the following expressions $$0.1 \leq x < 0.8,$$

$$0.4 \leq y \leq 0.8,$$

$$2 \leq m < 10$$

said amorphous aluminum hydroxide gel being produced by the process which comprises reacting an aluminum compound soluble in water and/or lower alcohols selected from the group consisting of aluminum chloride, aluminum nitrate, aluminum sulfate, aluminum metal, aluminum ammonium sulfate, aluminum bromide, aluminum fluoride, aluminum potassium sulfate, aluminum isopropoxide, sodium aluminate, potassium aluminate, and aluminum sodium sulfate, with a carbonate ion yielding compound soluble in water and/or lower alcohols selected from the group consisting of sodium carbonate, potassium carbonate, sodium hydrogen carbonate and potassium hydrogen carbonate, at a pH of about 6 to about 9.5 under such conditions that the $CO_2/Al$ mole ratio of the resulting aluminum hydroxide gel is about 0.1–about 8, and ion exchanging the alkali metals of the resulting compound with magnesium and/or calcium.

2. An antacid composition comprising an antacid effective amount of an amorphous aluminum hydroxide gel as defined in claim 1 and a pharmaceutically acceptable diluent or carrier.

* * * * *